(12) United States Patent
Wang et al.

(10) Patent No.: US 8,624,030 B2
(45) Date of Patent: Jan. 7, 2014

(54) N-DEMETHYLATION OF 6-KETO MORPHINANS

(75) Inventors: Peter X. Wang, Creve Coeur, MO (US); Tao Jiang, Chesterfield, MO (US); David W. Berberich, St. Peters, MO (US); Subo Liao, Ballwin, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 266 days.

(21) Appl. No.: 13/196,929

(22) Filed: Aug. 3, 2011

(65) Prior Publication Data

US 2012/0035366 A1 Feb. 9, 2012

Related U.S. Application Data

(60) Provisional application No. 61/370,653, filed on Aug. 4, 2010.

(51) Int. Cl.
*C07D 489/02* (2006.01)
*C07D 489/08* (2006.01)

(52) U.S. Cl.
USPC .............................................. 546/45; 546/44

(58) Field of Classification Search
USPC ..................................................... 546/45, 44
See application file for complete search history.

(56) References Cited

U.S. PATENT DOCUMENTS 7,671,204 B2 * 3/2010 Wang et al. ..................... 546/46

OTHER PUBLICATIONS

Lewis J. Sargent et al.; "Agonists-Antagonists Derived from Desomophine and Metopon"; Journal of Medicinal Chemistry; 1970; pp. 1061-1063; vol. 13, No. 6.
Coop et al., "L-Selectride as a General Reagent for the O-Demethylation and N-Decarbomethoxylation of Opium Alkaloids and Derivatives", Journal of Organic Chemistry, 1998, pp. 4392-4396, vol. 63, No. 13.
Bartels-Keith, J.R.; "Synthesis Related to Northebaine. Part I. Northebaine and N-Allyl-northebaine", Journal of the Chemical Society; J. Chem. Society; 1966; pp. 617-624;.
International Search Report for PCT/US2011/046345, mailed Sep. 26, 2011.

* cited by examiner

*Primary Examiner* — Charanjit Aulakh

(57) ABSTRACT

The present invention provides processes for the demethylation of an N-methyl morphinan comprising a ketone functional group. In particular, the invention provides methods for the protection of the ketone functional group such that impurities are not generated during the demethylation of the N-methyl morphinan.

15 Claims, No Drawings

N-DEMETHYLATION OF 6-KETO MORPHINANS

CROSS REFERENCE TO RELATED APPLICATIONS

This application claims the benefit of U.S. Provisional Application No. 61/370,653 filed Aug. 4, 2010, which is incorporated herein in its entirety.

FIELD OF THE INVENTION

The present invention generally relates to the N-demethylation of a morphinan comprising a ketone functional group.

BACKGROUND OF THE INVENTION

N-demethylation of opiate derivatives is a necessary chemical step in the preparation of "NaI" products, including naltrexone and naloxone. All of the "NaI" compounds are prepared from nor-opiates (opiates contained an NH group) and are derived from natural opiates or their derivatives that have been N-demethylated. Therefore the conversion of an N-methyl functional group into an N-alkyl functional group via an NH functional group is an important transformation process in the production of opiates.

One of the current processes for the N-demethylation of an opiate containing a ketone group is to convert the opiate into an alkyloxy- or aryloxy-carbonyl opiate, followed by its hydrolysis to form a nor-opiate. For example, oxycodone is converted into ethoxycarbonyl-noroxycodone, and the subsequent hydrolysis of ethoxycarbonyl-noroxycodone with either a strong acid or a strong base forms noroxycodone. However, the transformation is accompanied with the formation of aldol dimer impurities that are extremely difficult to remove from the desired product. Thus, there is a need for improved processes for the N-demethylation of opiates comprising ketone groups such that the formation of aldol dimer impurities is minimized or eliminated.

SUMMARY OF THE INVENTION

The present invention provides processes for demethylating 6-keto morphinans such that substantially no aldol dimer impurities are formed Briefly, therefore, one aspect of the present invention encompasses a process for demethylating an N-methyl morphinan comprising a 6-ketone group. The process comprises protecting the 6-ketone group by forming an alkene acetal, a dialkyl acetal, or an enol ether group at carbon 6, and then removing the N-methyl group by contact with a hydrocarbyl haloformate to form a 6-ketone-protected, N-hydrocarboxycarbonyl morphinan.

Another aspect of the invention provides a process for preparing a compound comprising Formula (III) from a compound comprising Formula (I). The process comprises (a) contacting the compound comprising Formula (I) with an agent that forms a ketone protecting group such that a compound comprising Formula (II) is formed, and (b) contacting the compound comprising Formula (II) with an N-demethylating agent comprising LC(O)OZ and a proton acceptor to form the compound comprising Formula (III) according to the following reaction scheme:

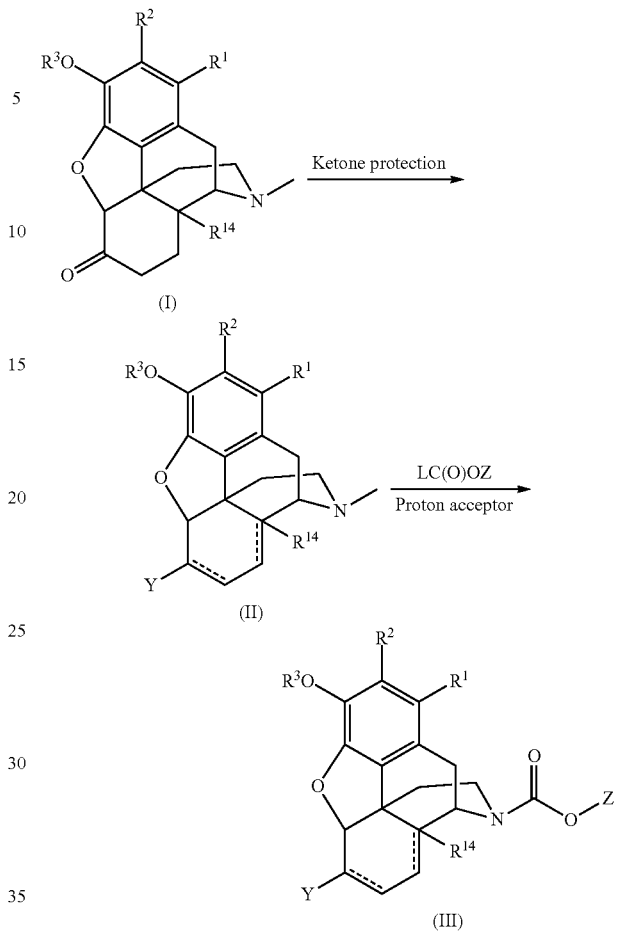

wherein:
- $R^1$ and $R^2$ are independently chosen from hydrogen, halogen, hydroxy, amino, cyano, {—}$OR^8$, hydrocarbyl, and substituted hydrocarbyl;
- $R^3$ is chosen from hydrogen, hydrocarbyl, and substituted hydrocarbyl;
- $R^{14}$ is chosen from hydrogen, halogen, hydroxy, {—}$OR^8$, hydrocarbyl, and substituted hydrocarbyl;
- $R^8$ and Z are independently chosen from hydrocarbyl and substituted hydrocarbyl;
- L is halogen; and
- Y is chosen from alkene acetal, dialkyl acetal, and enol ether, wherein each dashed line indicates an optional double bond.

Other features and iterations of the invention are described in more detail below.

DETAILED DESCRIPTION OF THE INVENTION

Disclosed herein are processes by which N-methyl morphinans comprising 6-ketone functional groups may be demethylated such that substantially no aldol dimer impurities are formed. In particular, methods are disclosed for protecting the 6-ketone group prior to the demethylation reaction. Consequently, the demethylated morphinans may be readily purified and isolated without having to perform elaborate purification procedures to remove aldol dimer impurities.

(I) Processes for the N-Demethylation of 6-Ketone Morphinans

One aspect of the invention encompasses a process for demethylating an N-methyl morphinan comprising a 6-ketone group. The process comprises protecting the 6-ketone group by forming an alkene acetal, a dialkyl acetal, or an end ether group at carbon 6 such that a 6-ketone-protected, N-methyl morphinan is formed. The process further comprises removing the N-methyl group by contacting the 6-ketone-protected, N-methyl morphinan with a hydrocarbyl haloformate to form a 6-ketone-protected, N-hydrocarboxycarbonyl morphinan.

In general, the morphinans detailed herein include any compound comprising a morphinan structure as diagrammed below. For the purposes of

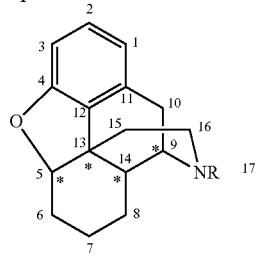

illustration, the ring atoms of the core morphinan structure are numbered as diagrammed below, wherein R is hydrogen, hydrocarbyl or substituted hydrocarbyl:

Morphinan compounds have asymmetric centers. In particular, the core morphinan compound may have at least four chiral carbons (designated by asterisks); namely, C-5, C-13, C-14, and C-9.

(II) Processes for the Preparation of Compounds Comprising Formula (III) from Compounds Comprising Formula (I)

In another embodiment of the invention, an N-hydrocarboxycarbonyl morphinan compound comprising Formula (III) is prepared from a 6-ketone, N-methyl morphinan comprising Formula (I). The process comprises contacting the compound comprising Formula (I) with an agent that forms a ketone protecting group such that a compound comprising Formula (II) is formed. The process further comprises contacting the compound comprising Formula (II) with an N-demethylating agent comprising LC(O)OZ and a proton acceptor to form the compound comprising Formula (III). Since the ketone functional group is protected during the N-demethylation reaction, substantially no aldol dimer impurities are formed. Moreover, as detailed below, the compound comprising Formula (III) may be converted into a nor-morphinan compound by contact with a nucleophile, and the ketone protecting groups may be removed by contact with a proton donor. For purposes of illustration, Reaction Scheme 1 depicts the synthesis of the compound comprising Formula (III) in accordance with this aspect of the invention:

Reaction Scheme 1:

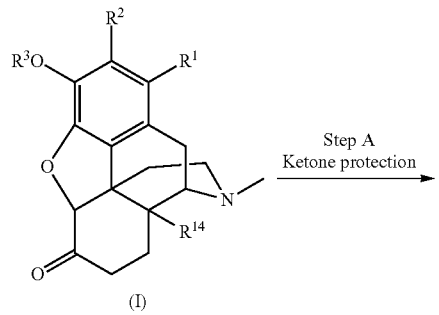

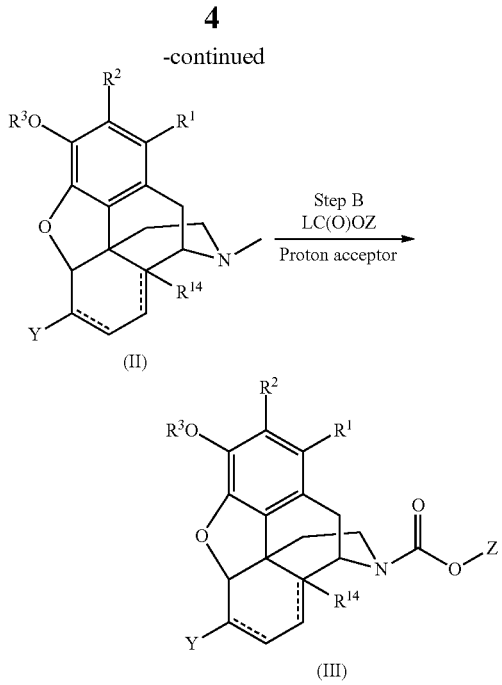

wherein:
- $R^1$ and $R^2$ are independently chosen from hydrogen, halogen, hydroxy, amino, cyano, {—}$OR^8$, hydrocarbyl, and substituted hydrocarbyl;
- $R^3$ is chosen from hydrogen, hydrocarbyl, and substituted hydrocarbyl;
- $R^{14}$ is chosen from hydrogen, halogen, hydroxy, {—}$OR^8$, hydrocarbyl, and substituted hydrocarbyl;
- $R^8$ and Z are independently chosen from hydrocarbyl and substituted hydrocarbyl;
- L is halogen; and
- Y is chosen from alkene acetal, dialkyl acetal, and enol ether, wherein each dashed line indicates an optional double bond.

In one embodiment, $R^1$, $R^2$, and $R^{14}$ are independently chosen from hydrogen, halogen, hydroxyl, alkyoxy, acyl, alkyl, alkenyl, aryl, substituted alkyl, substituted alkenyl, substituted aryl, alkoxycarbonyl, and aroxycarbonyl. In a preferred embodiment, $R^1$ and $R^2$ are hydrogen, and $R^{14}$ is hydrogen, hydroxyl, or protected hydroxyl. In another embodiment, $R^3$ is chosen from hydrogen, alkyl, alkenyl, aryl, substituted alkyl, substituted alkenyl, substituted aryl, acyl, alkoxycarbonyl, aryloxycarbonyl, acetal, ether, silyl ether, and alkylsulfonyl. Preferably, $R^3$ is hydrogen, methyl, or an oxygen protecting group. In a further embodiment, Y is ethylene acetal, propylene acetal, dimethyl acetal, diethyl acetal, methyl enol ether, or ethyl enol ether. In yet another embodiment, Z is chosen from alkyl, alkenyl, alkylaryl, aralkyl, aryl, substituted alkyl, substituted alkenyl, substituted alkylaryl, substituted aralkyl, and substituted aryl. Preferred Z groups include alkyl, methyl, ethyl, propyl, isopropyl, butyl, isobutyl, tert-butyl, phenyl, benzyl, methoxymethyl, vinyl, and 2-chloroethyl. Even more preferred Z groups are alkyl and phenyl.

In a preferred embodiment, $R^1$ and $R^2$ are hydrogen; $R^3$ is hydrogen, methyl, or an oxygen protecting group; $R^{14}$ is hydrogen, hydroxy, or protected hydroxy; Y is ethylene acetal, dimethyl acetal, or methyl enol ether; and Z is alkyl or phenyl.

(a) Step a of the Process

The process commences with protection of the 6-ketone group of the compound comprising Formula (I) by contact with an agent that forms a ketone protecting group. As detailed above, the ketone protecting group may be an alkene acetal, a dialkyl acetal, or an enol ether. The formation of each type of ketone protecting group is described below.

(i) Alkene Acetal

In one embodiment, the compound comprising Formula (I) may be an alkene acetal comprising Formula (Ia):

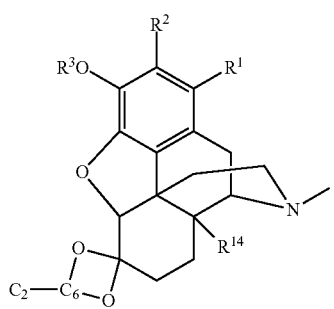

(IIa)

wherein:
$R^1$, $R^2$, $R^3$, and $R^{14}$ are as defined above.

To form the compound comprising Formula (IIa), the compound comprising Formula (I) may be contacted with an alkene diol and a proton donor. In general, the alkene diol comprises from about 2 to 6 carbon atoms. Non-limiting examples of suitable alkene diols include ethanediol, propanediol, a butanediol, a pentanediol, and a hexanediol. In exemplary embodiments, the alkene diol may be ethylene glycol (i.e., ethane-1,2-diol) or propylene glycol (i.e., propane-1,2-diol).

The amount of alkene diol contacted with the compound comprising Formula (I) can and will vary. In general, the molar ratio of the compound comprising Formula (I) to the alkene diol may range from about 1:1 to about 1:50. In various embodiments, the molar ratio of the compound comprising Formula (I) to the alkene diol may be about 1:1, 1:2, 1:3, 1:4, 1:5, 1:6, 1:8, 1:10, 1:15, 1:20, 1:25, 1:30, 1:35, 1:40, or 1:50. In an exemplary embodiment, the molar ratio of the compound comprising Formula (I) to the alkene diol may range from about 1:4 to about 1:30.

A variety of proton donors are suitable for use in this process. In general, the proton donor has a pKa of less than about 0. Non-limiting examples of proton donors having this characteristic include hydrogen halides (e.g., hydrochloric acid (HCl), hydrobromic acid (HBr), hydroiodic acid (HI), and the like); halogen oxoacids (e.g., chloric acid ($HClO_3$), perchloric acid ($HClO_4$), and corresponding compounds for bromine and iodine); sulfuric acid ($H_2SO_4$); fluorosulfuric acid ($FSO_3H$); nitric acid ($HNO_3$), fluoroantimonic acid; fluoroboric acid; hexafluorophosphoric acid; chromic acid; boric acid; and sulfonic acids (e.g., methanesulfonic acid (or mesylic acid, $CH_3SO_3H$), ethanesulfonic acid (or esylic acid, $CH_3CH_2SO_3H$), benzenesulfonic acid (or besylic acid, $C_6H_5SO_3H$); p-toluenesulfonic acid (or tosylic acid, $CH_3C_6H_4SO_3H$), trifluoromethanesulfonic acid (or triflic acid, $CF_3SO_3H$), and so forth). In an exemplary embodiment, the proton donor may be methanesulfonic acid.

The molar ratio of the compound comprising Formula (I) to the proton donor may vary. In general, the molar ratio of the compound comprising Formula (I) to the proton donor may range from about 1:0.1 to about 1:10. In some embodiments, the molar ratio of the compound comprising Formula (I) to the proton donor may be about 1:0.1, 1:0.25, 1:0.5, 1:1, 1:1.5, 1:2, 1:2.5, 1:3, 1:3.5, 1:4, 1:4.5, 1:5, 1:6, 1:7, 1:8, 1:9, or 1:10. In an exemplary embodiment, molar ratio of the compound comprising Formula (I) to the proton donor may be about 1:3.

(ii) Dialkyl Acetal

In another embodiment, the compound comprising Formula (II) may be a dialkyl acetal comprising Formula (IIb):

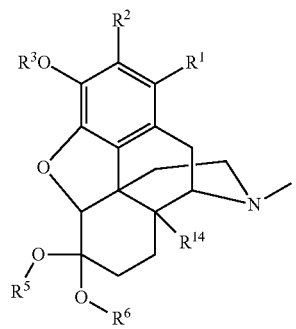

(IIb)

wherein:
$R^1$, $R^2$, $R^3$, and $R^{14}$ are as defined above; and
$R^5$ and $R^6$ are hydrocarbyl or substituted hydrocarbyl.

In preferred embodiments, $R^5$ and $R^6$ are independently alkyl or substituted alkyl, wherein the alkyl comprises from 1 to 8 carbon atoms.

To form the compound comprising Formula (IIb), the compound comprising Formula (I) may be contacted with at least one alcohol and a proton donor. Typically, the at least one alcohol may be an alkanol comprising from 1 to 8 carbon atoms. Suitable alkanols include, without limit, methanol, ethanol, n-propanol, isopropanol, butanols, pentanols, and the like.

The amount of alcohol that is contacted with the compound comprising Formula (I) can and will vary. In general, the molar ratio of the compound comprising Formula (I) to the alcohol may range from about 1:1 to about 1:300. In certain embodiments, the molar ratio of the compound comprising Formula (I) to the alcohol may range from about 1:1 to about 1:5, from about 1:5 to about 1:25, from about 1:25 to about 1:100, or from about 1:100 to about 1:300. In an exemplary embodiment, the molar ratio of the compound comprising Formula (I) to the alcohol may range from about 1:150 to about 1:200, or more preferably about 1:180.

A variety of proton donor may be used to prepare the compound comprising Formula (IIb). In general, the proton donor may have a pKa of less than about 0. Suitable proton donors are listed above in section (II)(a)(i).

The amount of proton donor contacted with the compound comprising Formula (I) may vary. In general, the molar ratio of the compound comprising Formula (I) to the proton donor may range from about 1:0.1 to about 1:5. In various embodiments, the molar ratio of the compound comprising Formula (I) to the proton donor may be about 1:0.1, 1:0.2, 1:0.3, 1:0.4, 1:0.5, 1:0.6, 1:0.8, 1:1, 1:1.5, 1:2, 1:2.5, 1:3, 1:3.5, 1:4, 1:4.5, or 1:5. In an exemplary embodiment, the molar ratio of the compound comprising Formula (I) to the proton donor may range from about 1:1 to about 1:1.5, or more preferably about 1:1.05.

(iii) Enol Ether

In a further embodiment, the compound comprising Formula (II) may be an enol ether comprising Formula (IIc):

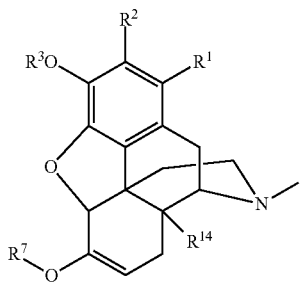

(IIc)

wherein:
$R^1$, $R^2$, $R^3$, and $R^{14}$ are as defined above; and
$R^7$ is hydrocarbyl or substituted hydrocarbyl.

In preferred embodiments, $R^7$ is alkyl or substituted alkyl, wherein the alkyl comprises from 1 to 8 carbon atoms.

The compound comprising Formula (IIc) may be formed by either of two methods. First, the compound comprising Formula (IIc) may be formed by contacting the compound comprising Formula (I) with an alcohol and a proton donor essentially as detailed above in section (II)(a)(ii), followed by distillation of the alcohol. Those of skill in the art are familiar with suitable distillation techniques. Second, the compound comprising Formula (IIc) may be formed by contacting the compound comprising Formula (I) with a proton acceptor and a dialkyl sulfate.

A variety of proton acceptors are suitable for use in preparation of the compound comprising Formula (IIc). In general, the proton acceptor has a pKa greater than about 13, or more preferably greater than about 20. Non-limiting examples of suitable proton acceptors having this characteristic include hydroxides of alkali metals and alkaline earth metals (such as, for example, NaOH and Ca(OH)$_2$ and the like), as well as group 1 salts of carbanions, alkyl amides, and hydrides (such as, for example, butyl lithium, lithium methyl amide, lithium isopropyl amide, sodium hydride, sodium borohydride, and the like). In an exemplary embodiment, the proton acceptor may be sodium hydride.

The amount of proton acceptor used in the process can and will vary. In general, the molar ratio of the compound comprising Formula (I) to the proton acceptor may range from about 1:1 to about 1:3. In certain embodiments, the molar ratio of the compound comprising Formula (I) to the proton acceptor may be about 1:1.0, 1:1.2, 1:1.4, 1:1.5, 1:1.6, 1:1.8, 1:2.0, 1:2.2, 1:2.4, 1:2.6, 1:2.8, or 1:3.0. In an exemplary embodiment, the molar ratio of the compound comprising Formula (I) to the proton acceptor may be about 1:1.5.

The identity of the dialkyl sulfate used to prepare the compound comprising Formula (IIc) can and will vary. Non-limiting examples of suitable dialkyl sulfates include dimethyl sulfate, diethyl sulfate, dipropyl sulfate, diisopropyl sulfate, dibutyl sulfate, dipentyl sulfate, and dibenzyl sulfate. In an exemplary embodiment, the dialkyl sulfate may be dimethyl sulfate.

The amount of dialkyl sulfate used to prepare the compound comprising Formula (IIc) may vary. In general, the molar ratio of the compound comprising Formula (I) to the dialkyl sulfate may range from about 1:1 to about 1:3. In various embodiments, the molar ratio of the compound comprising Formula (I) to the dialkyl sulfate may be about 1:1.0, 1:1.2, 1:1.4, 1:1.6, 1:1.8, 1:2.0, 1:2.2, 1:2.4, 1:2.6, 1:2.8, or 1:3.0. In an exemplary embodiment, the molar ratio of the compound comprising Formula (I) to the dialkyl sulfate may be about 1:1.4.

(iv) Solvent

For each of the reactions detailed above in sections (II)(a) (i), (ii), and (iii), the reaction is conducted in the presence of a solvent. Suitable solvents include nonpolar solvents, aprotic polar solvents, and combinations thereof. Non-limiting examples of suitable nonpolar solvents include benzene, butyl acetate, tert-butyl methyl ether, chlorobenzene, chloroform, chloromethane, cyclohexane, dichloromethane, dichloroethane, di-tert-butyl ether, dimethyl ether, diethylene glycol, diethyl ether, diglyme, diisopropyl ether, ethyl tert-butyl ether, ethylene oxide, fluorobenzene, heptane, hexane, methyl tert-butyl ether, toluene, and combinations thereof. Suitable aprotic solvents include, without limit, acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), 1,4-dioxane, ethyl acetate, ethyl formate, formamide, hexachloroacetone, hexamethylphosphoramide, methyl acetate, N-methylacetamide, methylethyl ketone, methylisobutyl ketone, N-methylformamide, methylene chloride, methoxyethane, morpholine, nitrobenzene, nitromethane, propionitrile, propyl acetates, sulfolane, tetramethylurea, tetrahydrofuran (THF), 2-methyl tetrahydrofuran, tetrahydropyran, trichloromethane, and combinations thereof. In preferred embodiments, the solvent may be dimethylformamide (DMF), or dimethyl sulfoxide (DMSO).

The amount of solvent added to the reaction mixture can and will vary. In general, the molar ratio of the solvent to the compound comprising Formula (I) may range from about 0.5:1 to about 100:1. In various embodiments, the molar ratio of the solvent to the compound comprising Formula (I) may range from 0.5:1 to about 5:1, from about 5:1 to about 25:1, or from about 25:1 to about 100:1. In preferred embodiments, the molar ratio of the solvent to the compound comprising Formula (I) may range from about 0.5:1 to about 20:1.

(v) Reaction Conditions

In general, the reactions detailed above in (i), (ii), and (iii) may be conducted at a temperature that ranges from about 0° C. to about 60° C. In various embodiments, the reaction may be conducted at a temperature that ranges from about 0° C. to 10° C., from about 10° C. to about 20° C., from about 20° C. to about 30° C., from about 30° C. to about 40° C., or from about 40° C. to about 60° C. In exemplary embodiment, the temperature of the reaction may be less than about 40° C. The reaction is generally performed under ambient pressure.

Typically, the reaction is allowed to proceed for a sufficient period of time until the reaction is complete, as determined by chromatography (e.g., HPLC). In this context, a "completed reaction" generally means that the reaction mixture contains a significantly diminished amount of the compound comprising Formula (I), and a significantly increased amount of the compound comprising Formula (II) compared to the amounts of each present at the beginning of the reaction. Typically, the amount of the compound comprising Formula (I) remaining in the reaction mixture after the reaction is complete may be less than about 3%, and preferably less than about 1%. In general, the reaction may proceed for about 2 minutes to about 8 hours. In certain embodiments, the reaction may be allowed to proceed for about 5, 10, 20, 30, 40, 50 or 60 minutes, or for about 1.5, 2, 2.5, 3, 3.5, 4, 4.5, 5, 6, 7, or 8 hours.

The compound comprising Formula (II) may be isolated from the reaction mixture using techniques known to those of skill in the art. Non-limiting examples of suitable techniques include precipitation, extraction, evaporation, distillation, chromatography, and crystallization.

The yield of the compound comprising Formula (II) can and will vary. Typically, the yield of the compound comprising Formula (II) may be at least about 65%. In one embodiment, the yield of the compound comprising Formula (II) may range from about 65% to about 75%. In another embodiment, the yield of the compound comprising Formula (II) may range from about 75% to about 85%. In a further embodiment, the yield of the compound comprising Formula (II) may range from about 85% to about 95%. In still another embodiment, the yield of the compound comprising Formula (II) may be greater than about 95%.

(b) Step B of the Process

The process further comprises removing the N-methyl group of the ketone protected compound comprising Formula (II). For this, the compound comprising Formula (II) is contacted with an N-demethylating agent comprising LC(O)OZ and a proton acceptor, each of which are detailed below, to form the compound comprising Formula (III).

(i) N-demethylating Agent Comprising LC(O)Oz

A variety of N-demethylating agents are suitable for use in this process. In general, the N-demethylating agent will be a hydrocarbyl haloformate having the formula LC(O)OZ, wherein L and Z are as defined above. In a preferred embodiment, L may be chloro or bromo, and Z may be methyl, ethyl, propyl, isopropyl, butyl, isobutyl, tert-butyl, phenyl, benzyl, methoxymethyl, vinyl, or 2-chloroethyl. In preferred embodiments, the N-demethylating agent may be an alkyl haloformate (e.g., methyl chloroformate, methyl bromoformate, ethyl chloroformate, ethyl bromoformate, propyl chloroformate, propyl bromoformate, isopropyl chloroformate, isopropyl bromoformate, butyl chloroformate, butyl bromoformate, isobutyl chloroformate, isobutyl bromoformate, and the like), an alkoxyalkyl haloformate (e.g., methyoxymethyl chloroformate, methyoxymethyl bromoformate, ethoxymethyl chloroformate, ethoxymethyl bromoformate, and so forth), benzyl haloformate, phenyl haloformate, vinyl haloformate, or 2-chloroalkyl haloformate. In general, the alkyl comprises from one to eight carbon atoms. In exemplary embodiments, the N-demethylating agent may be an alkyl chloroformate, phenyl chloroformate, benzyl chloroformate, vinyl chloroformate, or 2-chloroalkyl chloroformate.

The molar ratio of the compound comprising Formula (II) to the N-demethylating agent can and will vary depending. In general, the molar ratio of the compound comprising Formula (II) to the N-demethylating agent to may range from about 1:1 to about 1:3. In various embodiments, the molar ratio of the compound comprising Formula (II) to the N-demethylating agent may be about 1:1.0, 1:1.1, 1:1.2, 1:1.3, 1:1.4, 1:1.5, 1:1.6, 1:1.7: 1:1.8, 1:1.9, 1:2.0, 1:2.1, 1:2.2. 1:2.3, 1:2.4. 1:2.5, 1:2.6, 1:2.7, 1:2.8, 1:2.9, or 1:3.0. In an exemplary embodiment, the molar ratio of the compound comprising Formula (II) to the N-demethylating agent may be about 1:1.2.

(ii) Proton Acceptor

To facilitate the N-demethylation of the compound comprising Formula (II), the reaction is typically carried out in the presence of a proton acceptor. In general, the proton acceptor has a pKa of between about 7 and about 13, preferably between about 8 and about 10. Representative proton acceptors that may be employed include, but are not limited to, borate salts (such as, for example, $Na_3BO_3$), di- and tri-basic phosphate salts (such as, for example, $Na_2HPO_4$ and $Na_3PO_4$), bicarbonate salts (such as, for example, $NaHCO_3$, $KHCO_3$, mixtures thereof, and the like), hydroxide salts (such as, for example, NaOH, KOH, mixtures thereof, and the like), carbonate salts (such as, for example, $Na_2CO_3$, $K_2CO_3$, mixtures thereof, and the like), organic bases (such as, for example, pyridine, triethylamine, diisopropylethylamine, N-methylmorpholine, N,N-dimethylaminopyridine, and mixtures thereof), organic buffers (such as, for example, N-(2-acetamido)-2-aminoethane sulfonic acid (ACES), N-(2-acetamido)-iminodiacetic acid (ADA), N,N-bis(2-hydroxyethyl)glycine (BICINE), 3 (cyclohexylamino)-1-propanesulfonic acid (CAPS), 2 (cyclohexylamino) ethanesulfonic acid (CHES),4-(2-hydroxyethyl)-1-piperazinepropanesulfonic acid (EPPS),4-(2-hydroxyethyl) piperazine-1-ethanesulfonic acid (HEPES), 2 (4 morpholinyl)ethanesulfonic acid (MES),4-morpholinepropanesulfonic acid (MOPS), 1,4-piperazinediethanesulfonic acid (PIPES), [(2-hydroxy-1,1-bis(hydroxymethyl)ethyl) amino]-1-propanesulfonic acid (TAPS), 2-[(2-hydroxy-1,1-bis(hydroxymethyl)ethyl)amino]ethanesulfonic acid (TES), salts and/or mixtures thereof, and the like), and combinations thereof. When the proton acceptor is an organic buffer, the organic buffer preferably lacks a hydroxy-substituted nitrogen atom, as this substituent may compete for reaction with a hydrocarbyl haloformate reactant. In one embodiment, the proton acceptor is chosen from $NaHCO_3$, $KHCO_3$, $K_2CO_3$, NaOH, KOH, and mixtures thereof. In a preferred embodiment, the proton acceptor is $NaHCO_3$, $KHCO_3$, or a combination thereof.

The molar ratio of the compound comprising Formula (II) to the proton acceptor may range from about 1:1 to about 1:6. In some embodiments, the molar ratio of the compound comprising Formula (II) to the proton acceptor may be about 1:1, 1:1.5, 1:2, 1:2.5, 1:3, 1:3.5, 1:4, 1:4.5, 1:5, 1:5.5, or 1:6. In an exemplary embodiment, the molar ratio of the compound comprising Formula (II) to the proton acceptor may range from about 1:2 to about 1:3.

(iii) Solvent

The reaction is generally conducted in the presence of a solvent. The solvent may be a nonpolar organic solvent or a polar aprotic solvent. Representative nonpolar solvents include, but are not limited to, alkane and substituted alkane solvents (including cycloalkanes), aromatic hydrocarbons, esters, ethers, ketones, and combinations thereof. Specific nonpolar solvents that may be employed include, for example, benzene, butyl acetate, t-butyl methylether, t-butyl methylketone, chlorobenzene, chloroform, cyclohexane, dichloromethane, dichloroethane, diethyl ether, ethyl acetate, fluorobenzene, heptane, hexanes, isobutylmethylketone, methylethylketone, methylisobutyl ketone, pentyl acetate, propyl acetates, toluene, and combinations thereof. Non-limiting examples of suitable aprotic solvents include acetone, acetonitrile, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMAC), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride, methoxyethane, morpholine, nitrobenzene, nitromethane, propionitrile, sulfolane, tetramethylurea, tetrahydrofuran (THF), 2-methyl tetrahydrofuran, tetrahydropyran, trichloromethane, and combinations thereof. In an exemplary embodiment, the solvent may be chloroform, ethyl acetate, or acetonitrile.

In general, the molar ratio of the solvent to the compound comprising Formula (II) will range from about 0.5:1 to about 100:1. In various embodiments, the molar ratio of the solvent to the compound comprising Formula (II) may range from 0.5:1 to about 5:1, from about 5:1 to about 25:1, or from about 25:1 to about 100:1. In preferred embodiments, the molar ratio of the solvent to the compound comprising Formula (II) may range from about 0.5:1 to about 20:1. In an exemplary embodiment, the molar ratio of the solvent to the compound comprising Formula (II) may range from about 2:1 to about 10:1.

(iv) Reaction Conditions

In general, the reaction will be conducted at a temperature that ranges from about 0° C. to about 120° C., or more preferably from about 20° C. to about 80° C. In various embodiments, the demethylation reaction may be conducted at about 30° C., about 40° C., about 50° C., about 55° C., about 60° C., about 65° C. about 70° C., about 75° C., or about 80° C. The reaction is typically performed under ambient pressure, and preferably in an inert atmosphere (e.g., nitrogen or argon).

Typically, the reaction is allowed to proceed for a sufficient period of time until the reaction is complete, as defined above. Typically, the amount of the compound comprising Formula (II) remaining in the reaction mixture after the reaction is complete may be less than about 3%, and preferably less than about 1%. In general, the reaction may proceed for about 1 hour to about 24 hours, and more typically, for about 2 hours to about 8 hours.

The compound comprising Formula (III) may be isolated from the reaction mixture using techniques known to those of skill in the art. Non-limiting examples of suitable techniques include precipitation, extraction, evaporation, distillation, chromatography, and crystallization.

The yield of the compound comprising Formula (III) can and will vary. Typically, the yield of the compound comprising Formula (III) may be at least about 40%. In one embodiment, the yield of the compound comprising Formula (III) may range from about 40% to about 60%. In another embodiment, the yield of the compound comprising Formula (III) may range from about 60% to about 80%. In a further embodiment, the yield of the compound comprising Formula (III) may range from about 80% to about 90%. In still another embodiment, the yield of the compound comprising Formula (III) may be greater than about 90%, or more preferably greater than about 95%.

Importantly the compound comprising Formula (III) contains substantially no aldol dimer impurities. In general, the compound comprising Formula (III) comprises less than about 0.05% by weight of an aldol dimer impurity. In some embodiments, the level of the aldol dimer impurity is less than about 0.01%, less than about 0.005%, or less than about 0.001%.

(c) Hydrolysis of N-hydrocarboxycarbonyl Group

The process may further comprise contacting the compound comprising Formula (III) with a nucleophile such that the N-hydrocarboxycarbonyl group is cleaved to form a compound comprising Formula (IV). Reaction Scheme 2 illustrates this reaction process:

Reaction Scheme 2:

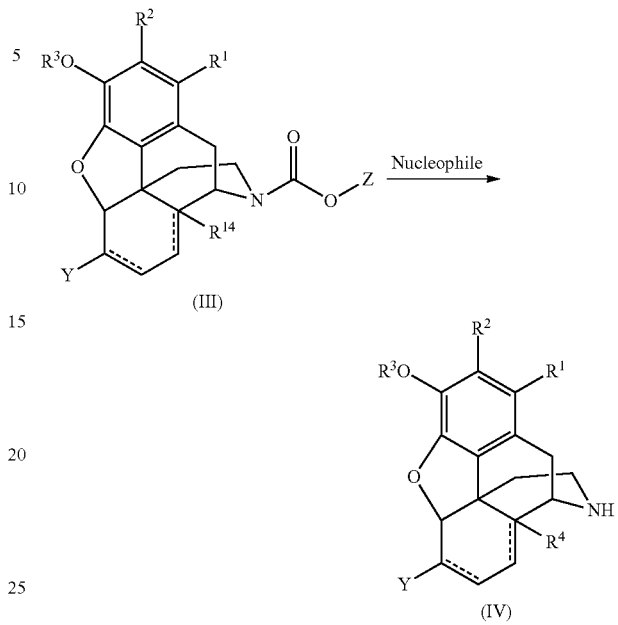

A variety of nucleophiles are suitable for use in this step of the process. In general, the nucleophile may have a pKa greater than about 13. Nucleophiles having this characteristic include hydroxides of alkali metals and alkaline earth metals (such as, for example, NaOH and $Ca(OH)_2$ and the like); alkoxides (such as, e.g., methoxide, ethoxide, and so forth); group 1 salts of carbanions (such as, e.g., methyl lithium, butyl lithium, and so forth); amides (such as, e.g., sodium amide, lithium methylamide, lithium isopropyl amide, and the like); and hydrides (such as, for example, sodium hydride, $NaBH_4$, and the like). In preferred embodiments, the nucleophile may be potassium hydroxide or sodium hydroxide.

The amount of nucleophile added to the reaction mixture can and will vary. In general, the molar ratio of the compound comprising Formula (III) to the nucleophile may range from about 1:1 to about 1:8. In various embodiments, the molar ratio of the compound comprising Formula (III) to the nucleophile may be about 1:1, 1:1.5, 1:2, 1:2.5, 1:3, 1:3.5, 1:4, 1:4.5, 1:5, 1:5.5, 1:6, 1:6.5, 1:7, 1:7.5, or 1:8. In an exemplary embodiment, the ratio of the compound comprising Formula (III) to the nucleophile may be about 1:4.

Contact with the nucleophile may be performed in the presence of a solvent. Suitable solvents are detailed above in section (II)(b)(iii). In some embodiments, the solvent may further comprise a protic solvent. Non-limiting examples of suitable protic solvents include water; an alcohol such as methanol, ethanol, isopropanol, n-propanol, isobutanol, n-butanol, s-butanol, t-butanol, and the like; a dial such as propylene glycol; an organic acid such as formic acid, acetic acid, and so forth; an amide such as formamide, acetamide, and the like; and combinations of any of the above.

The hydrolysis step may be conducted at a temperature that ranges from about 50° C. to about 100° C. In various embodiments, the temperature of the reaction may be 50° C., 55° C., 60° C., 65° C., 70° C., 75° C., 80° C., 85° C., 90° C., 95° C., or 100° C. In preferred embodiments, the reaction may be conducted at a temperature that ranges form about 60° C. to about 90° C.

Typically, the reaction is allowed to proceed for a sufficient period of time until the reaction is complete, as detailed above. In a completed reaction, the amount of the compound comprising Formula (III) remaining in the reaction mixture may be less than about 3%, and preferably less than about 1%. In general, the reaction may proceed for about 1 hour to about 12 hours, and more typically, for about 2 hours to about 6 hours.

The compound comprising Formula (IV) may be isolated from the reaction mixture using techniques known to those of skill in the art. Non-limiting examples of suitable techniques include precipitation, extraction, evaporation, distillation, chromatography, and crystallization. The compound comprising Formula (IV) may be used as is, or may be converted to another compound using techniques familiar to those of skill in the art.

The yield of the compound comprising Formula (IV) can and will vary. Typically, the yield of the compound comprising Formula (IV) may be at least about 35%. In one embodiment, the yield of the compound comprising Formula (IV) may range from about 35% to about 65%. In another embodiment, the yield of the compound comprising Formula (IV) may range from about 65% to about 75%. In yet another embodiment, the yield of the compound comprising Formula (IV) may range from about 75% to about 85%. In a further embodiment, the yield of the compound comprising Formula (IV) may range from about 85% to about 95%. In still another embodiment, the yield of the compound comprising Formula (IV) may be greater than about 95%.

(d) Removal of Ketone Protecting Groups

The compound comprising Formula (IV) also may be contacted with a proton donor such that the ketone protecting group is removed to form a compound comprising Formula (V), as diagrammed below in Reaction Scheme 3:

Reaction Scheme 3:

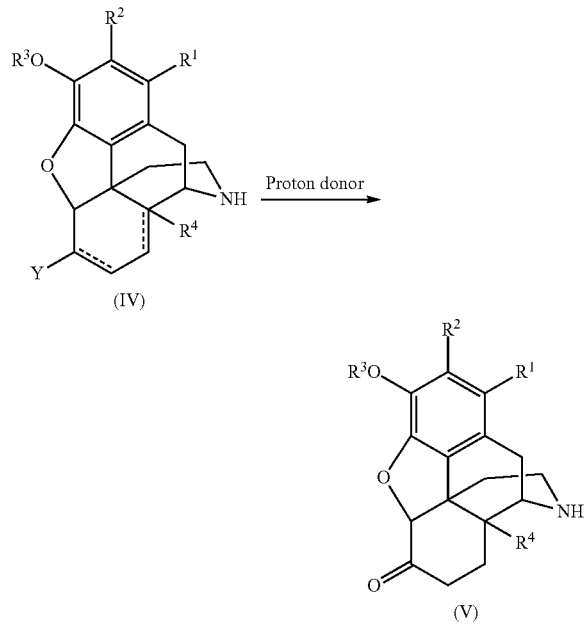

A variety of proton donors are suitable for use in this reaction. In general, the proton donor may have a pKa less than 0, or more preferably less than −2. Non-limiting examples of proton donors having this characteristic include hydrogen halides (e.g., hydrochloric acid (HCl), hydrobromic acid (HBr), hydroiodic acid (HI), and the like); halogen oxoacids (e.g., chloric acid ($HClO_3$), perchloric acid ($HClO_4$), and corresponding compounds for bromine and iodine); sulfuric acid ($H_2SO_4$); fluorosulfuric acid ($FSO_3H$); nitric acid ($HNO_3$), fluoroantimonic acid; fluoroboric acid; hexafluorophosphoric acid; chromic acid; boric acid; and sulfonic acids (e.g., methanesulfonic acid (or mesylic acid, $CH_3SO_3H$), ethanesulfonic acid (or esylic acid, $CH_3CH_2SO_3H$), benzenesulfonic acid (or besylic acid, $C_6H_5SO_3H$); p-toluenesulfonic acid (or tosylic acid, $CH_3C_6H_4SO_3H$), trifluoromethanesulfonic acid (or triflic acid, $CF_3SO_3H$), and so forth). In preferred embodiments, the proton donor may be hydrochloric acid (HCl) or hydrobromic acid (HBr).

The amount of proton donor contacted with the compound comprising Formula (IV) can and will vary. In general, the molar ratio of the compound comprising Formula (IV) to the proton donor may range from about 1:2 to about 1:10. In various embodiments, the molar ratio of the compound comprising Formula Op to the proton donor may be about 1:2, 1:2.5, 1:3, 1:3.5, 1:4, 1:4.5, 1:5, 1:5.5, 1:6, 1:6.5, 1:7, 1:7.5, 1:8, 1:9, or 1:10. In an exemplary embodiment, the ratio of the compound comprising Formula (IV) to the proton donor may be about 1:5.5.

Contact with the proton donor may be performed in the presence of a solvent. Suitable solvents are detailed above in section (II)(c). The reaction may be conducted at a temperature that ranges from about 25° C. to about 80° C. In various embodiments, the temperature of the reaction may be 25° C., 30° C., 35° C., 40° C., 45° C., 50° C., 55° C., 60° C., 65° C., 70° C., 75° C., or 80° C. In preferred embodiments, the reaction may be conducted at a temperature that ranges form about 40° C. to about 50° C.

Typically, the reaction is allowed to proceed for a sufficient period of time until the reaction is complete, as detailed above. In a completed reaction, the amount of the compound comprising Formula (IV) remaining in the reaction mixture may be less than about 3%, and preferably less than about 1%. In general, the reaction may proceed for about 30 minutes to about 12 hours.

The compound comprising Formula (V) may be isolated from the reaction mixture using techniques known to those of skill in the art. Non-limiting examples of suitable techniques include precipitation, extraction, evaporation, distillation, chromatography, and crystallization. The compound comprising Formula (V) may be used as is, or may be converted to another compound using techniques familiar to those of skill in the art.

The yield of the compound comprising Formula (V) can and will vary. Typically, the yield of the compound comprising Formula (V) may be at least about 35%. In one embodiment, the yield of the compound comprising Formula (V) may range from about 35% to about 65%. In another embodiment, the yield of the compound comprising Formula (V) may range from about 65% to about 75%. In yet another embodiment, the yield of the compound comprising Formula (V) may range from about 75% to about 85%. In a further embodiment, the yield of the compound comprising Formula (V) may range from about 85% to about 95%. In still another embodiment, the yield of the compound comprising Formula (V) may be greater than about 95%.

(e) Stereochemistry

The compounds comprising any of Formulas (I), (II), (IIa), (IIb), (IIc), (III), (IV), or (V) may have a (−) or a (+) orientation with respect to the rotation of polarized light. More specifically, each chiral center of the morphinans may have an R or an S configuration. The compounds described herein may have at least four chiral centers, namely carbons C-5, C-9, C-13, and C-14. At each chiral center, the stereochemistry at the carbon atom is independently R or S. The configuration of C-5, C-9, C-13, and C-14, respectively, may be RRRR, RRRS, RRSR, RSRR, SRRR, RRSS, RSSR, SSRR, SRRS, SRSR, RSRS, RSSS, SRSS, SSRS, SSSR, or SSSS, provided that the C-15 and C-16 atoms are both on the alpha face of the molecule or both on the beta face of the molecule.

The compound comprising any of Formulas (I), (II), (IIa), (IIb), (IIc), (III), (IV), or (V) may be a free base or a pharmaceutically acceptable salt. Pharmaceutically acceptable salts include, without limitation, acetate, aspartate, benzoate, bitartrate, citrate, formate, gluconate, glucuronate, glutamate, fumarate, hydrochloride, hydrobromide, hydroiodide, hypophosphite, isobutyrate, isocitrate, lactate, malate, maleate, meconate, methylbromide, methanesulfonate, monohydrate, mucate, nitrate, oxalate, phenylpriopionate, phosphate, phthalate, propionate, pyruvate, salicylate, stearate, succinate, sulfate, tannate, tartrate, terephthalate, valerate, and the like.

Definitions

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include fury, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "oxygen protecting group" as used herein denotes a group capable of protecting an oxygen atom (and hence, forming a protected hydroxy), wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl(TBDPS) and the like. A variety of protecting groups and the synthesis thereof may be found in "Protective Groups in Organic Synthesis" by T. W. Greene and P. G. M. Wuts, $3^{rd}$ ed., John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocycle, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Synthesis of
Dihydro-Cyclic-Ethylene-Acetal-Codeinone

Hydrocodone (306 g) was suspended in ethylene glycol (1224 mL) and cooled to 5~10° C. MeSO$_3$H (108.3 mL) was added to form a solution while maintaining the reaction mixture below 40° C. The reaction mixture was stirred at room temperature for 4 h. The solution was added to icy cool 3% NH$_4$OH (6120 mL) with stirring to form a suspension. It was stirred at 0-10° C. for 2 h and filtered. The resultant solids were washed with water (3×153 mL) and dried under vacuum at 60° C. for 24 h to give 327 g of solid.

Example 2

Synthesis of Dihydrocyclic-Ethylene-Acetal-N-(Ethoxycarbonyl)-Norcodeinone

The above dihydro-cyclic-ethylene-acetal-codeinone (327 g) was dissolved in CHCl$_3$ (1308 mL). Na$_2$CO$_3$ (505 g) and MgSO$_4$ (109 g) were added. The mixture was heated to 55° C. Ethyl chloroformate (363 mL) was added. The reaction mixture was heated with reflux for 6 h, cooled down to room temperature, and filtered. The solids obtained were washed with CHCl$_3$ (2×327 mL). The filtrate was treated with 5% aqueous solution of NaOH (1635 mL). The aqueous layer was separated and extracted with CHCl$_3$ (327 mL). The combined organic layers were washed with 0.1 N HCl (1635 mL) and water (1635 mL). The organic layer was pumped down to dryness to give the product as solids.

Example 3

Synthesis of Dihydrocyclic-Ethylene-Acetal-N-(Phenoxycarbonyl)-Norcodeinone

To the cooled mixture of dihydro-cyclic-ethylene-acetal-codeinone (32.4 g), sodium bicarbonate (23.8 g), and chloroform (145 mL) in an ice bath (pre-cooled for 10 min) was added phenylchloroformate (14.2 mL) dropwise. The resulting mixture was gradually heated to 53° C. for three hrs; then the reaction was cooled to room temperature; and the mixture was filtered. The solid material was washed with CHCl$_3$ (2×20 mL). The filtrates were added to ice-cooled 5% Na$_2$CO$_3$ aqueous solution (145 mL). The aqueous phase was extracted with CHCl$_3$ (3×100 mL). The combined organic layers were washed with water (2×100 mL). The organic layer was evaporated on rotar-vapor and gave a foam solid, 44.7 g.

Example 4

Synthesis of Dihydrothebaine

To the solution of dihydrocodone (5.7 g) and dry DMF (66 mL) was added sodium hydride in 60% mineral oil (0.9 g). The resulting light yellow mixture was stirring under nitrogen for 15 min and then cooled to 0° C. in ice bath for 10 minutes; dimethyl sulfate (2.4 mL) was then added to the cooled light yellow mixture and stirred for 30 min. The reaction was poured into ice/water mixture (250 mL) and the product was extracted with ethyl acetate (400 mL); the organic phase was separated and washed with 1% ammonium hydroxide brine (50 mL×5), and dried over anhydrous sodium sulfate. After removing the volatiles, a oil residue was left. The crude material was purified on silica gel with 3:1:1 EtOAc/Heptane/DCM+1% Et$_3$N+1% MeOH. The final product was obtained white solid, 2.8 g.

Example 5

Synthesis of
Dihydro-N-(Phenoxycarbonyl)-Northebaine

To the cooled mixture of dihydrothebaine (30 g), sodium bicarbonate (29 g) and 216 mL of acetonitrile in ice bath was added dropwise phenylchloroformate (24 mL). After finishing the addition, the reaction mixture was gradually heated to 50° C. (oil bath) for five hrs. The reaction was then cooled to room temperature, and to the cooled reaction was added 500 mL ethyl acetate and 200 mL water; the organic phase was separated and washed with 2 N sodium hydroxide (4×150 mL), water (200 mL), followed by 5% formic acid solution (2×60 mL) and brine, and then dried over anhydrous magnesium sulfate. After removing the volatiles, it gave 42 g of light purple solid.

Example 6

Synthesis of Dihydrocyclic-Ethylene-Acetal-Norcodeinone

The above dihydrocyclic-ethylene-acetal-N-(ethoxycarbonyl)-norcodeinone was heated and dissolved in DMSO (981 mL) and ethylene glycol (196 mL) under nitrogen. Water (196 mL) and KOH (50%, 327 mL) were added. The mixture was heated at 100° C. for 10 h. More water (5886 mL) was added and heated for another 1 h after complete addition. It was allowed to cooled down to rt and stirred at rt for 2 h and filtered. The solids obtained were washed with water (3×327 mL), dried in vacuum at 80° C. for 6 h to give 287 g solids.

Example 7

Synthesis of Dihydrocyclic-Ethylene-Acetal-Norcodeinone Hydrochloride Salt

A mixture of dihydrocyclic-ethylene-acetal-N-(phenoxycarbonyl)-norcodeinone (5 g), toluene (19 mL), dimethyl sulfoxide (4 mL) and potassium hydroxide (2.3 g) was heated to 86° C. (oil bath) for five hrs, then the reaction was cooled to 30-35° C. and quenched by addition of water (11 mL); the resulting mixture stirred at rt overnight. To the reaction mixture was added 150 mL methylene chloride, the organic phase was separated; the aqueous phase was extracted with methylene chloride (50 mL×2). The combined organic extracts were washed with dilute ammonia hydroxide once and dried over anhydrous magnesium sulfate. After removing volatiles, to the residue was added 100 mL toluene, bubbled the solution in ice bath with hydrogen chloride gas, plenty of white precipitates were formed. The resulting mixture was stirred in ice bath for two hrs, the solid was filtered and washed with toluene, dried in air overnight and further dried in vacuum oven at 60° C. to give 2.91 g of white solid.

Example 8

Synthesis of Dihydrocyclic-Ethylene-Acetal-Norcodeinone Hydrochloride Salt

A mixture of dihydrocyclic-ethylene-acetal-N-(phenoxycarbonyl)-norcodeinone (5 g), toluene (19 mL), dimethyl acetamide (4 mL) and potassium hydroxide (2.3 g) was heated to 86° C. (oil bath) for two hrs, then the reaction was cooled to room temperature and quenched by addition of water (30 mL). The product was extracted with dichloromethane (3×60 mL). The combined organic extracts were washed with dilute ammonia hydroxide once and dried over anhydrous magnesium sulfate. After removing volatiles, to the residue was added 100 mL toluene, bubbled the solution in ice bath with hydrogen chloride gas, plenty of white precipitates were formed. The resulting mixture was stirred in ice bath for two hrs, the solid was filtered and washed with toluene, dried in air overnight and further dried in vacuum oven at 60° C. to give 2.7 g of white solid.

Example 9

Synthesis of Dihydrocyclic-Ethylene-Acetal-Norcodeinone Hydrochloride Salt

A mixture of starting material dihydrocyclic-ethylene-acetal-N-(phenoxycarbonyl)-norcodeinone (5 g), toluene (19 mL), tetramethylene sulfone (4 mL) and potassium hydroxide (2.3 g) was heated to 86° C. (oil bath) for three hrs, then the reaction was cooled to room temperature and quenched by addition of water (30 mL). The product was extracted with dichloromethane (3×60 mL). The combined organic extracts were washed with dilute ammonia hydroxide once and dried over anhydrous magnesium sulfate. After removing volatiles, to the residue was added 80 mL toluene, bubbled the solution in ice bath with hydrogen chloride gas, plenty of white precipitates were formed. The resulting mixture was stirred in ice bath for two hrs, the solid was filtered and washed with toluene, dried in air overnight and further dried in vacuum oven at 60° C., it gave 3.0 g white solid.

Example 10

Synthesis of Nordihydrothebaine

A mixture of dihydro-N-(phenoxycarbonyl)northebaine (10 g), toluene (43 mL), DMSO (11 mL), and potassium hydroxide (10.8 g) was heated to 86° C. (oil bath) for five hrs. the reaction was cooled to room temperature and to the cooled reaction was added 100 mL water. The organic phase was separated and was washed with water (2×30 mL); the aqueous washings were combined with the aqueous phase; the combined aqueous phases were extracted with 1:9 MeOH/dichloromethane (4×70 mL); the organic phases were combined and washed with 2N sodium hydroxide solution (4×50 mL), then dried over anhydrous sodium sulfate. After removing the volatiles on rotavapor, the residue was further dried in vacuum at 60° C. for 12 hrs, it gave 2.2 g of light yellow solid.

Example 11

Synthesis of 3-Bromo-Dihydrocycic-Ethylene-Acetal-Norcodeinone

Dihydrocyclic-ethylene-acetal-norcodeinone (275 g) was dissolved in chloroform (1375 mL) and ethylene glycol (186 mL) and cooled down to 0-10° C. MeSO$_3$H (87 mL) was added to form a solution while maintaining the reaction temperature below 15° C. during the addition. NBA (115.6 g, 1 eq) was added over 3 h at 0-10° C. The solution was stirred for 30 min and transferred into an icy cooled solution of 5% NH$_4$OH (1100 mL). The aqueous layer was extracted with chloroform (275 mL). The combined organic layer was washed with water (2×825 mL), pumped down to dryness to give the crude product as solids.

Example 12

Synthesis of 3-Bromo-Norhydrocodone Hydrobromide

To the above solids, 3-bromo-dihydrocyclic-ethylene-acetal-norcodeinone, was dissolved in a solution of HBr in water (made from 510 mL of c-HBr and 1530 mL of water). It was heated at 40° C. for 40 min, cooled down to 5° C. for 3 h, and filtered. The solids obtained were washed with cool solution of 5% HBr in water (3×170 mL, 5° C.), dried in vacuum at 60° C. for 18 h to give 335 g solids. The product contained no aldol dimer.

Example 13

Synthesis of Norhydrocodone Hydrobromide

Dihydrocyclic-ethylene-acetal-N-norcodeinone (10 g) was dissolved in a solution of HBr in water (made from 12 mL of c-HBr and 38 mL of water). I t was heated at 40° C. for 40 min, cooled down to 5° C. for 3 h, and filtered. The solids obtained were washed with cool solution of 5% HBr in water (2×4 mL, 5° C.), dried in vacuum at 60° C. for 18 h to give 6.8 g of solids.

Example 14

Synthesis of Norhydrocodone

To the suspension of nordihydrothebaine (2.4 g) in 50 mL water was added 25 mL of 1.25 M HCl in methanol and the resulting solution was stirred at room temperature for 30 min. The volatiles of the reaction were removed on a rotavapor to yield 2.3 g of yellow solid.

What is claimed is:

1. A process for preparing a compound of Formula (III) from a compound of Formula (I), the process comprising:
   a) contacting the compound of Formula (I) with an agent that forms a ketone protecting group such that a compound of Formula (II) is formed; and
   b) contacting the compound of Formula (II) with an N-demethylating agent comprising LC(O)OZ and a proton acceptor to form the compound of Formula (III);

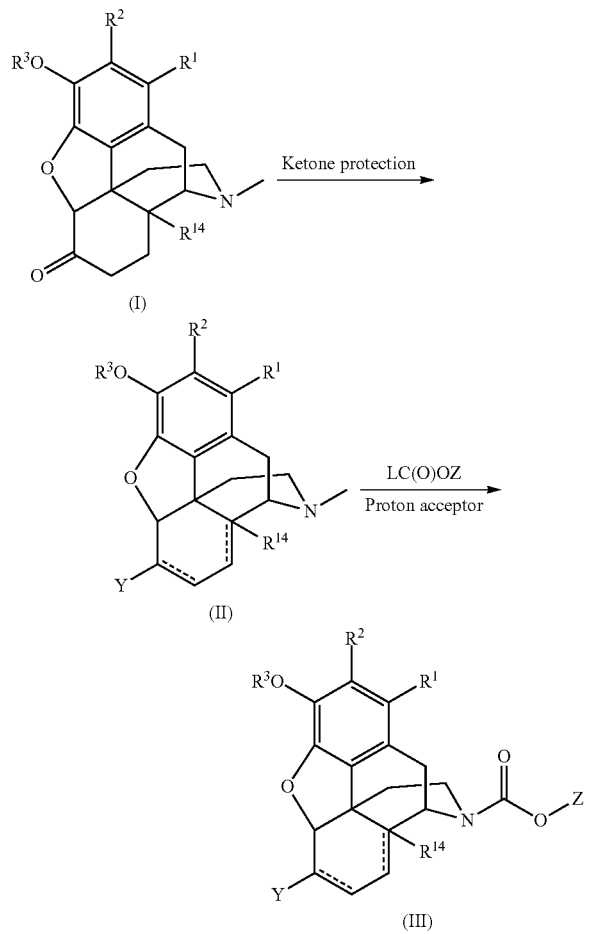

wherein:
R$^1$ and R$^2$ are independently chosen from hydrogen, halogen, hydroxy, amino, cyano, {—}OR$^8$, hydrocarbyl, and substituted hydrocarbyl;

R$^3$ is chosen from hydrogen, hydrocarbyl, and substituted hydrocarbyl;

R$^{14}$ is chosen from hydrogen, halogen, hydroxy, {—}OR$^8$, hydrocarbyl, and substituted hydrocarbyl;

R$^8$ and Z are independently chosen from hydrocarbyl and substituted hydrocarbyl;

L is halogen; and

Y is chosen from alkene acetal, dialkyl acetal, and enol ether, wherein each dashed line indicates an optional double bond.

2. The process of claim 1, wherein:
R$^1$, R$^2$, and R$^{14}$ are independently chosen from hydrogen, halogen, hydroxy, alkyoxy, acyl, alkyl, alkenyl, aryl, substituted alkyl, substituted alkenyl, substituted aryl, alkoxycarbonyl, and aroxycarbonyl;

R$^3$ is chosen from hydrogen, alkyl, alkenyl, aryl, substituted alkyl, substituted alkenyl, substituted aryl, acyl, alkoxycarbonyl, aroxycarbonyl, acetal, ether, silyl ether, and alkylsulfonyl; and Z is chosen from alkyl, alkenyl, alkylaryl, aralkyl, aryl, substituted alkyl, substituted alkenyl, substituted alkyiaryl, substituted aralkyl, and substituted aryl.

3. The process of claim 1, wherein the compound of Formula (II) is chosen from:
   (a) an alkene acetal of Formula (IIa) that is formed by contacting the compound of Formula (I) with an alkene diol and a proton donor, the compound of Formula (IIa) having the structure:

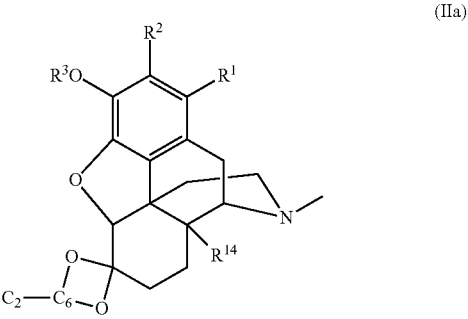

wherein:
R$^1$ and R$^2$ are independently chosen from hydrogen, halogen, hydroxy, amino, cyano, {—}OR$^8$, hydrocarbyl, and substituted hydrocarbyl;

R$^3$ is chosen from hydrogen, hydrocarbyl, and substituted hydrocarbyl;

R$^{14}$ is chosen from hydrogen, halogen, hydroxy, {—}OR$^8$, hydrocarbyl, and substituted hydrocarbyl; and R$^8$ is chosen from hydrocarbyl and substituted hydrocarbyl;

(b) a dialkyl acetal of Formula (IIb) that is formed by contacting the compound of Formula (I) with at least one alcohol and a proton donor, the compound of Formula (IIb) having the structure:

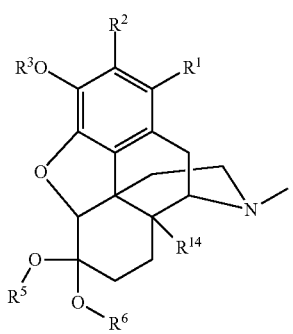

(IIb)

wherein:
R¹ and R² are independently chosen from hydrogen, halogen, hydroxy, amino, cyano, {—}OR⁸, hydrocarbyl, and substituted hydrocarbyl;
R³ is chosen from hydrogen, hydrocarbyl, and substituted hydrocarbyl;
R¹⁴ is chosen from hydrogen, halogen, hydroxy, {—}OR⁸, hydrocarbyl, and substituted hydrocarbyl; and
R⁵, R⁶, and R⁸ are independently chosen from hydrocarbyl and substituted hydrocarbyl; and
(c) an enol ether of Formula (IIc) that is formed either a) by contacting the compound of Formula (I) with an alcohol and a proton donor followed by distillation of the alcohol, or b) by contacting the compound of Formula (I) with a proton acceptor and a dialkyl sulfate, the compound of Formula (IIc) having the structure:

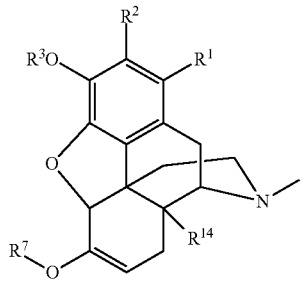

(IIc)

wherein:
R¹ and R² are independently chosen from hydrogen, halogen, hydroxy, amino, cyano, {—}OR⁸, hydrocarbyl, and substituted hydrocarbyl;
R³ is chosen from hydrogen, hydrocarbyl, and substituted hydrocarbyl;
R¹⁴ is chosen from hydrogen, halogen, hydroxy, {—}OR⁸, hydrocarbyl, and substituted hydrocarbyl; and
R⁷ and R⁸ are independently chosen from hydrocarbyl and substituted hydrocarbyl.

4. The process of claim 1, wherein the reaction of step (a) is conducted in the presence of an aprotic solvent, a nonpolar solvent, or combinations thereof; the weight ratio of the solvent to the compound of Formula (I) is from about 0.5:1 to about 20:1; the reaction of step (a) is conducted at a temperature from about 0° C. to about 60° C.; the N-demethylating agent is chosen from alkyl haloformate, alkoxyalkyl haloformate, phenyl haloformate, benzyl haloformate, vinyl haloformate, and 2-chloroalkyl haloformate; the proton acceptor has a pKa greater than about 7; the molar ratio of the compound of Formula (II) to LC(O)OZ to the proton acceptor is from about 1:1:1 to about 1:3:6; the reaction of step (b) is conducted in the presence of a solvent chosen from acetonitrile, chlorobenzene, chloroform, 1,2-dichloroethane, ethyl acetate, n-propyl acetate, isopropyl acetate, tetrahydrofuran, toluene, and combinations thereof; the weight ratio of the solvent to the compound of Formula (II) is from about 0.5:1 to about 20:1; and the reaction of step (b) is conducted at a temperature from about 0° C. to about 120° C.

5. The process of claim 1, wherein the compound of Formula (III) comprises less than about 0.05% by weight of an aldol dimer impurity.

6. The process of claim 1, wherein the compound of Formula (III) has a yield of at least about 40% by weight.

7. The process of claim 1, further comprising contacting the compound of Formula (III) with a nucleophile to form a compound of Formula (IV):

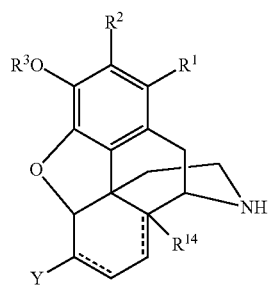

(IV)

wherein:
R¹ and R² are independently chosen from hydrogen, halogen, hydroxy, amino, cyano, {—}OR⁸, hydrocarbyl, and substituted hydrocarbyl;
R³ is chosen from hydrogen, hydrocarbyl, and substituted hydrocarbyl;
R¹⁴ is chosen from hydrogen, halogen, hydroxy, {—}OR⁸, hydrocarbyl, and substituted hydrocarbyl;
R⁸ is hydrocarbyl or substituted hydrocarbyl; and
Y is chosen from cyclic alkene acetal, dialkenol acetal, and enol ether, wherein each dashed line indicates an optional double bond.

8. The process of claim 7, wherein the nucleophile is chosen from an amide, an alkoxide, a hydride, and a hydroxide; and the molar ratio of the compound of Formula (III) to the nucleophile is from about 1:1 to about 1:8.

9. The process of claim 7, further comprising contacting the compound of Formula (IV) with a proton donor to form a compound of Formula (V):

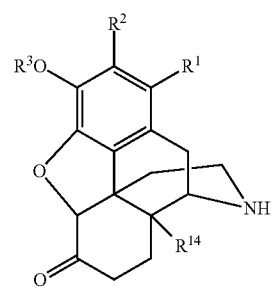

(V)

wherein:
- $R^1$ and $R^2$ are independently chosen from hydrogen, halogen, hydroxy, amino, cyano, {—}$OR^8$, hydrocarbyl, and substituted hydrocarbyl;
- $R^3$ is chosen from hydrogen, hydrocarbyl, and substituted hydrocarbyl;
- $R^{14}$ is chosen from hydrogen, halogen, hydroxy, {—}$OR^8$, hydrocarbyl, and substituted hydrocarbyl; and
- $R^8$ is hydrocarbyl or substituted hydrocarbyl.

10. The process of claim 9, wherein the proton donor has a pKa of less than about −2; and the molar ratio of the compound of Formula (IV) to the proton donor is about 1:2 to about 1:10.

11. The process of claim 1, wherein the optical activity of the compounds of Formulas (I), (II), or (III) is chosen from (−) enantiomer, (+) enantiomer, and combinations thereof; and the configuration of C-5, C-13, C-14, and C-9, respectively, is chosen from RRRR, RRRS, RRSR, RSRR, SRRR, RRSS, RSSR, SSRR, SRRS, SRSR, RSRS, RSSS, SRSS, SSRS, SSSR, and SSSS, provided that C-15 and C-16 are both either on the alpha face or the beta face of the molecule.

12. The process of claim 3, wherein the alkene diol is ethylene glycol; the proton donor is methanesulfonic acid; the molar ratio of the compound of Formula (I) to ethylene glycol to methanesulfonic acid is about 1:4-30:3; and the reaction of step (a) is conducted at a temperature of less than about 40° C.

13. The process of claim 3, wherein the proton acceptor is sodium hydride; the dialkyl sulfate is dimethyl sulfate; the molar ratio of the compound of Formula (I) to the proton acceptor to the dialkyl sulfate is about 1:1.5:1.4; and the reaction of step (a) is conducted at a temperature of less than about 40° C.

14. The process of 12, wherein the N-demethylating agent is ethyl chloroformate or phenyl chloroformate; the proton acceptor is a carbonate or bicarbonate salt; the molar ratio of the compound of Formula (II) to the demethylating agent to the proton acceptor is from about 1:1.2:2-3; the reaction of step (b) is conducted at a temperature from about 40° C. to about 80° C.; the compound of Formula (III) comprises less than about 0.05% by weight of an aldol dimer impurity; and the optical activity of the compounds of Formulas (I), (II), or (III) is chosen from (−) enantiomer, (+) enantiomer, and combinations thereof; and the configuration of C-5, C-13, C-14, and C-9, respectively, is chosen from RRRR, RRRS, RRSR, RSRR, SRRR, RRSS, RSSR, SSRR, SRRS, SRSR, RSRS, RSSS, SRSS, SSRS, SSSR, and SSSS, provided that C-15 and C-16 are both either on the alpha face or the beta face of the molecule.

15. The process of 13, wherein the N-demethylating agent is ethyl chloroformate or phenyl chloroformate; the proton acceptor is a carbonate or bicarbonate salt; the molar ratio of the compound of Formula (II) to the demethylating agent to the proton acceptor is from about 1:1.2:2-3; the reaction of step (b) is conducted at a temperature from about 40° C. to about 80° C.; the compound of Formula (III) comprises less than about 0.05% by weight of an aldol dimer impurity; and the optical activity of the compounds of Formulas (I), (II), or (III) is chosen from (−) enantiomer, (+) enantiomer, and combinations thereof; and the configuration of C-5, C-13, C-14, and C-9, respectively, is chosen from RRRR, RRRS, RRSR, RSRR, SRRR, RRSS, RSSR, SSRR, SRRS, SRSR, RSRS, RSSS, SRSS, SSRS, SSSR, and SSSS, provided that C-15 and C-16 are both either on the alpha face or the beta face of the molecule.

\* \* \* \* \*